United States Patent [19]

Barrett et al.

[11] 4,335,928
[45] Jun. 22, 1982

[54] HIGH VOLTAGE CONNECTOR FOR X-RAY EQUIPMENT

[75] Inventors: David M. Barrett, Brookfield; William D. Love, Waukesha; Joseph L. Donaldson, Milwaukee, all of Wis.

[73] Assignee: General Electric Company, Schenectady, N.Y.

[21] Appl. No.: 164,104

[22] Filed: Jun. 30, 1980

[51] Int. Cl.³ .............................................. H01R 4/00
[52] U.S. Cl. ................................. 339/94 C; 339/117 R
[58] Field of Search ................. 339/117 R, 111, 94 R, 339/94 C, 60 R, 60 C, 103 C

[56] References Cited

U.S. PATENT DOCUMENTS

| | | | |
|---|---|---|---|
| 3,107,135 | 10/1963 | Keil | 339/94 C X |
| 4,046,451 | 9/1977 | Juds et al. | 339/94 C |
| 4,173,385 | 11/1979 | Fenn et al. | 339/94 C |

*Primary Examiner*—John McQuade
*Assistant Examiner*—Frank H. McKenzie, Jr.
*Attorney, Agent, or Firm*—Ralph G. Hohenfeldt

[57] ABSTRACT

A high voltage cable connector has a flanged insulating sleeve terminating the cable. The sleeve inserts in an insulating receptacle with some clearance space around it for being occupied by a fluid dielectric medium. The receptacle has a flange which is axially spaced from the flange on the sleeve when the sleeve is fully inserted and secured in the receptacle. A ring element is sealed between the flanges. It defines an annular chamber which communicates with the dielectric medium filled clearance space. A compressible element such as a bellows or diaphragm is disposed in the chamber for accommodating thermal expansion and contraction of the medium or the connector assembly to allow sealing of the system to prevent loss of dielectric and thereby prevent formation of cavities in the medium which could cause electrical breakdown.

11 Claims, 6 Drawing Figures

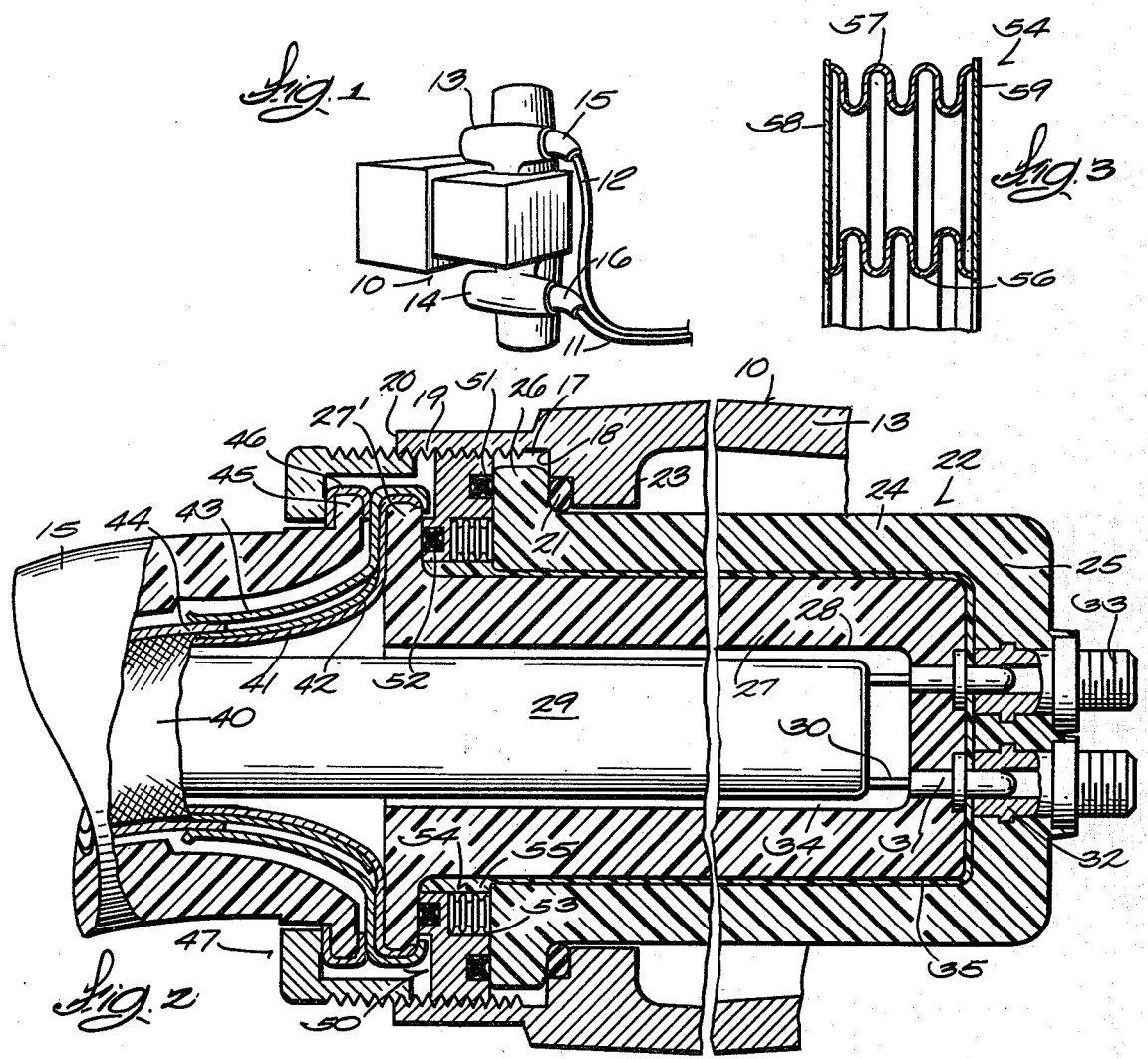
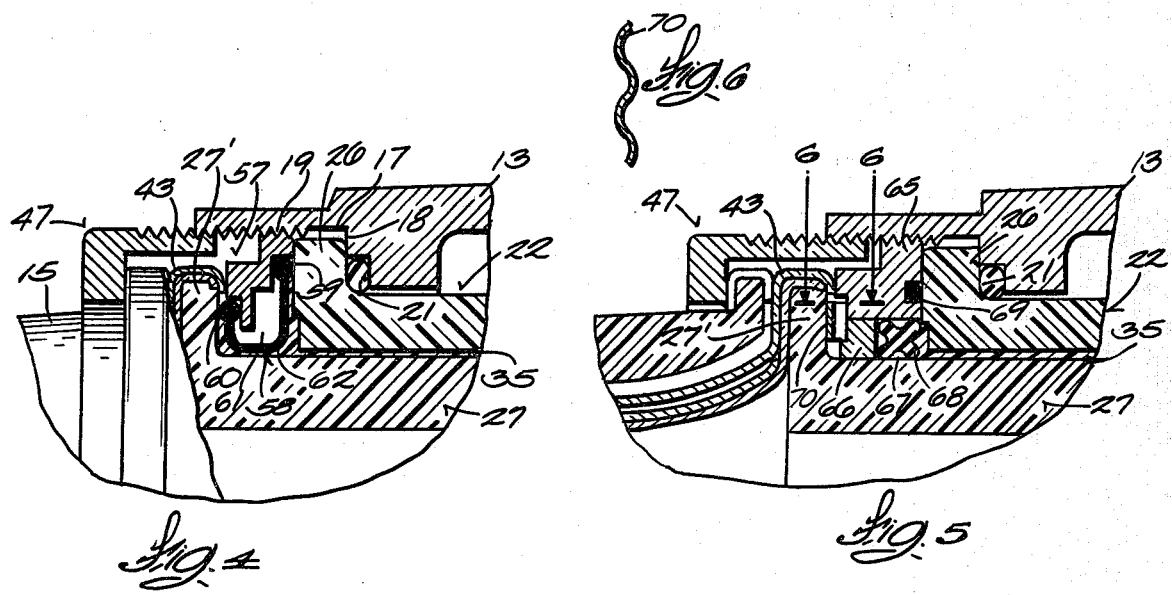

HIGH VOLTAGE CONNECTOR FOR X-RAY EQUIPMENT

This invention relates to connecting high voltage cables to electrical apparatus such as X-ray tubes, X-ray transformers, high voltage rectifiers and the like.

Medical X-ray systems commonly use voltages of up to 75 kilovolts peak (KVP) between respective power source terminals and ground. The type of cable connector generally used in such systems employs a female insulating receptacle on the X-ray tube or high voltage transformer and an insulating male sleeve which terminates the end of the high voltage cable and inserts in the receptacle to make an electrical connection. A fluid or viscous dielectric medium is used in the small clearance space between the receptacle and sleeve to displace air which would otherwise provide a path for high voltage arcing and breakdown.

Because X-ray tubes operate at high temperatures and are subject to almost universal orientation when in use, a non-melting and viscous silicone grease has been used customarily to fill the space between the receptacle and sleeve, instead of using a medium that would be fluid at any temperature, to minimize the likelihood of the medium leaking through the seals of the connector. Further, when a liquid or viscous dielectric medium is elevated from ambient temperature to the maximum expected operating temperature of the X-ray tube and its casing assembly, thermal expansion and contraction of the dielectric medium occurs to the extent of about 5% of its volume. Further, the material of which the male connector and female receptacle portions of the high voltage connector assembly are constructed also expand and contract in varying amounts upon heating and cooling thereby changing the volume to be filled by the dielectric grease.

The high viscosity of the various types of nonmelting electric media generally used in high temperature cable connectors make it difficult to assemble the cable terminal sleeve to the receptacle with a proper and adequate amount of dielectric medium between them and, as a practical matter, it is almost impossible to exclude air cavities from being entrapped in the dielectric medium. Even if air cavities could be excluded, experience has shown that when the connector and the dielectric medium heat expand some of the dielectric medium, being incompressible, is forced past the connector seals out of the interspace between plug and receptacle. Upon cooling, air is drawn into the interspace to replace the dielectric medium lost during heating. The minute air cavities thereby created provide high electrical intensity or stress regions which, in due course, lead to arcing, flashing and electrical breakdown along the clearance space between the outside of the cable terminal sleeve and the inside of the receptacle. In other words, current flows undesirably from the electrical connector pins on the male sleeve through air voids in the dielectric medium in the clearance, interspace and to ground by way of the metallic cable sheath.

SUMMARY OF THE INVENTION

The primary object of this invention is to provide a high voltage connector assembly which incorporates an effective seal against dielectric medium leakage and compensates for thermal expansion of the dielectric medium and the connector assembly so that conventional dielectric materials having a higher coefficient of thermal expansion such as oil or other low viscosity medium with a relatively low melting temperature such as petroleum jelly may be used to minimize the probability of air entrapment within the connector assembly. Moreover, the fundamental mechanism by which air voids, not present at assembly, but which are introduced by heating and cooling, is eliminated.

Briefly stated, the new sealing and dielectric medium expansion and contraction accommodating means is used with a connector comprised of a female insulating receptacle having one closed end in which there are connector pin receivers and an open end which is surrounded by a radially extending flange. One face of the flange interfaces with a shoulder in a counterbore in the apparatus which is to be connected with a cable. The cable is terminated with a male insulating sleeve that has connector pins in its end and fits with a small clearance space around it into the receptacle. The male sleeve is also provided with a radially outwardly extending integral flange which is in axial spaced relationship to the flange on the receptacle when the sleeve with the cable attached to it is inserted in the receptacle.

The insulating flanged female receptacle and the insulating male sleeve are basically conventional components of high voltage connectors. Employing seals between the flanges is also conventional. In accordance with the invention, however, an annular space or chamber is defined between the interfacing surfaces of the flange on the male sleeve and the flange on the receptacle. An annular resilient (compressible) element is disposed. The chamber is in fluid exchange communication with the clearance space between the sleeve and internal surface of the receptacle which is occupied by the dielectric medium. Thus, as the dielectric within the sealed region increases in volume when it heats, it compresses the resilient compressible element which is then loaded with a restorative force. When the dielectric medium cools and shrinks, the element expands under the influence of the force which is has stored and compensates for the dielectric volume decrease without creating air-filled cavities that would otherwise occur in the dielectric medium when it cools. The result is that no air-filled cavities nor vacuum pockets can occur in the dielectric medium.

How the foregoing and other more specific objects of the invention are achieved will be evident in the description of the illustrative embodiments of the invention which will now be set forth in reference to the drawing.

DESCRIPTION OF THE DRAWING

FIG. 1 is a perspective view of an X-ray tube casing to which a high voltage cable is connected with the new connector design shown in this figure and disclosed herein;

FIG. 2 shows a longitudinal section of a connector and cable assembly installed in an electrical apparatus such as an X-ray tube which is shown partially;

FIG. 3 is a cross section of a dielectric liquid expansion and contraction accommodating resilient element in the form of a toroidal bellows or diaphragm which is used in the connector assembly depicted in FIG. 2;

FIG. 4 is a fragmentary sectional view of an alternative embodiment of the new connector assembly;

FIG. 5 is another alternative embodiment of the connector assembly; and

FIG. 6 shows a side view of a resilient metallic wave spring which is used in the FIG. 5 embodiment and is viewed in the direction of the arrowheaded lines marked 6—6 in FIG. 5.

DESCRIPTION OF A PREFERRED EMBODIMENT

FIG. 1 depicts an X-ray tube casing 10 to which two insulated and metallically sheathed high voltage electric cables 11 and 12 may be connected by means of the new connector design which is to be described. In FIG. 1, the cable connectors are disposed within parts of the X-ray tube casing which are called horns 13 and 14. Each cable goes through an insulating strain relief sleeve such as those marked 15 and 16.

The preferred embodiment of the new cable connecting means is illustrated in FIG. 2. In this figure one of the casing horns is marked 13 as it is in FIG. 1. The casing is provided with a counterbore 17 which terminates in a shoulder 18 and has an internal thread 19 running from its open end 20 toward shoulder 18. The shoulder has an annular recess for accommodating an elastic o-ring 21 which is required because X-ray tube casing 10 is filled with dielectric fluid. A female receptacle 22 comprised of solid insulating material extends through an opening 23 in casing 13. This receptacle has a hollow cylindrical body 24 which has one end 25 closed and its opposite end open similar to a cup. Said opposite end has an integral radially outwardly extending flange 26 whose one face interfaces with and compresses o-ring 21 to effect a seal with the oil filled casing 13 when the parts of the connector are pressed together as will be explained.

The insulating male cable terminal member or sleeve which fits into insulating receptacle 22 is generally designated by the reference numeral 27. Sleeve 27 has an internal bore 28 into which the insulated and unsheathed end 29 of a high voltage cable is inserted. Sleeve 27 has a radially extending flange 27' molded integrally with one of its ends. A typical wire 30 extending from the end of the cable is fastened in a male connector pin, a typical pin being marked 31. The male pin connectors extend into female connectors 32 which are assembled and sealed into the closed end 25 of outer receptacle 22. Connectors 32 have threaded ends 33 for facilitating making electrical connections between them and whatever device, such as an X-ray tube, is being supplied from the cable. The space 34 around the cable in bore 28 is customarily filled with a self-setting insulating and sealing compound, not shown. The male terminal member or sleeve 27 can be and has been molded or potted directly on insulated cable end 29 in one connector style, not shown. In such case, space 34 is not created and a compound in this space is unnecessary. Term "sleeve" is used herein as inclusive of a male terminal member that is molded on the cable as well as one that is not.

It should be noted that there is a small clearance space or annular gap 35 defined between the outer periphery of male cable terminating sleeve 27 and the inner cylindrical surface of female receptacle 22. This clearance space is filled with a fluid dielectric medium to reduce the likelihood of an electrical breakdown between the cable connectors in the receptacle and the casing 13 in which it is mounted. As will be explained subsequently, the connector assembly described herein has a unique capability for accommodating expansion and contraction of the dielectric fluid medium in this clearance space, for maintaining effective seals against dielectric fluid leaking from the connector assembly and for eliminating vacuum or air pockets or cavities in the dielectric medium. Thus, in the present case, thin dielectric oil or synthetic dielectric liquid or a low viscosity material with a relatively low melting temperature such as certain silicone compounds and petroleum jelly may now be used as the dielectric medium in preference to conventional more viscous dielectrics. Being able to use a thin or relatively nonviscous dielectric medium facilitates inserting the male cable sleeve 27 into female receptacle 22 without having air pockets or cavities develop during assembly as well. It is only necessary to partially fill the receptacle 22 with the thin and flowable dielectric medium and let it ooze back along clearance gap 35 when male sleeve 27 is inserted in female receptacle 22. By way of example and not limitation, annular clearance space 35 between the receptacle and male sleeve is on the order of 10 to 12 thousandths of an inch in a commercial embodiment and the cylindrical part of the male sleeve is about five inches long.

For controlled expansion and contraction of the dielectric, it is desirable but not necessary for the receptacle 22 and sleeve 27 to have compatible thermal expansion properties. Thus, in a preferred commercial embodiment, female receptacle 22 and the sleeve 27 are made of an identical or similar molding compound.

In FIG. 2, the cable end 29 is shown extending into bore 28 of the male sleeve 27 but the braided metallic sheath 40 on the cable is flared out and soldered, in the region marked 41, to an annular conical metal ring 42 which is crimped around the outer periphery of the flange 27' extending from male cable terminating sleeve 27. Another ring or metal shield 43 is crimped over ring 42 and provides a gap in which the end of the outer plastic insulating sleeve 44 of the cable is squeezed and held. As mentioned in connection with FIG. 1, the cable passes through a rigid strain relief 15 which is also shown in FIG. 2. It has a flange 45 surrounded by a crimped-on ring 46 which provides a metal-to-metal bearing surface where it interferes with shield ring 43. An externally threaded ring nut 47 is turnable into the thread 19 within counterbore 17 in X-ray tube casing 10 for the purpose of clamping the male cable terminating sleeve 27 into female receptacle 22 as is evident from inspection of FIG. 2.

The flange 27' on male sleeve 27 and the flange 26 on female receptacle 22 are axially spaced from each other when the sleeve is inserted as far as it will go into the receptacle as is evident in FIG. 2. In accordance with this embodiment of the invention, the space between the interfacing surfaces of the flanges 27' and 26 has a ring element, generally designated by the reference numeral 50, disposed in it. Ring element 50 has a peripheral or external thread which turns into female thread 19 in tube casing counterbore 17 and acts to clamp the female receptacle 22 in the tube casing 13. The recesses in the ring element for enabling it to be tightened in with a spanner wrench are not shown. In the FIG. 2 embodiment, ring element 50 has grooves on its opposite end faces which are occupied by commercially available quad rings 51 and 52, which effect seals between the interfacing surfaces of the receptacle flange and sleeve flange, respectively. Ordinary o-rings could, of course, be used instead of quad rings. The quad rings may be neoprene rubber. They are efficient low pressure seals. Ring element 50 is also provided with an open-sided groove or chamber 53 which, in accordance with the invention, accommodates an element which yields or compresses when exposed to fluid pressure and tends to restore to its original volume as pressure is relieved. The compressible self-restoring element in the preferred FIG. 2 embodiment is a toroidal bellows 54 whose inside is contiguous with an annular cavity 55 which places the bellows in fluid exchange communication with dielectric medium filled clearance gap or space 35 between male sleeve 27 and female receptacle 22.

A magnified cross section through one side of annular or toroidal bellows 54 is shown in FIG. 3. Here it may be seen to comprise serpentine-shaped inner and outer rings 56 and 57 to which flat end plates 58 and 59 are brazed or welded. In a commercial embodiment, the bellows end plates 58 and 59 are made of stainless steel and the serpentine bellows walls are made of nickel. The bellows assembly as used in FIG. 2 is not required to perform any sealing function. It simply compresses when the dielectric medium in clearance space 35 becomes hot and expands and it expands to make up for contraction of the fluid when the fluid gets cooler to thereby prevent formation of air or vacuum cavities in the fluid. The bellows 54 may fit loosely in groove or chamber 53. In a commercial embodiment, the annular bellows 54 is not preloaded or precompressed and its interior is at atmospheric pressure when cold. When ring member 50 is turned in tightly, quad ring seal 51 becomes slightly compressed to effect a seal. When clamping ring nut 47 is screwed in, the other quad ring 52 becomes slightly compressed to effect a seal. Thus, all the volume change of the dielectric medium with temperature is accommodated exclusively by the bellows in this embodiment.

It should be evident that ring member 50 performs the multiple functions of retaining seals 51 and 52, clamping receptacle 22 and providing for development of the annular space or chamber 53 which is subject to the pressure of fluid in clearance space 35 and is occupied by compressible element 54. The arrangement permits using preexisting flanged female receptacles 22 and male sleeves 27 without modification. However, the chamber 53 does not have to be in clamping and seal retaining ring member 50. The annular space or chamber for accommodating compressible element 54 may be formed in the flange on female receptacle 22, for example, or it may be formed within the bore of the female receptacle or even as a groove in the outside of the sleeve. The requirements are that the dielectric fluid in the clearance space between the receptacle and the sleeve must be able to enter the chamber, the chamber should be internal to the receptacle and the chamber should be occupied by a compressible element.

The thermal expansion characteristics of the materials used for receptacle 22 and sleeve 27 should be chosen so the expansion of the sleeve will track expansion of the receptacle as the two components become warmer. If the sleeve expands at a higher rate, the volume of the fluid filled clearance space 35 decreases and pressures could build up which are higher than would be predicted if only the increase in temperature of the dielectric fluid itself were considered. Such high pressure, if they were allowed to occur, could cause the limits of the compressibility of the compressible element to be reached. By way of example, tests with a premanufacturing prototype revealed that pressures of the dielectric fluid at the highest operating temperatures expected in an X-ray tube casing environment reached a maximum of forty pounds per square inch whereas pressures were even higher in a prototype in which the sleeve expanded more than the receptacle.

Now that the preferred embodiment has been described in detail in connection with FIG. 2, alternative embodiments of the connector assembly will be described which use an annular resilient or compressible or yieldable element other than a bellows for accommodating volume changes in the dielectric medium.

In the FIG. 4 embodiment, components which are similar to those shown in FIG. 2 are given the same reference numerals. Thus, there is a casing 13 having a counterbore 17 which has an internal thread 19 and defines a shoulder 18 which provides for capturing an o-ring seal 21 between the shoulder and one face of the flange 26 on outer female insulating receptacle 22. It is assumed that the casing 13 is filled with oil which also surrounds receptacle 22. Shields such as the one marked 43 are crimped on the flange of inner male cable terminal sleeve 27. A clamping nut 47 is also provided for securing the sleeve in the receptacle.

In the FIG. 4 embodiment, flange 26 on the female receptacle 22 and flange 27' on male cable terminating sleeve 27 are axially spaced from each other when the sleeve is inserted as far as it will go into the receptacle. A metal ring member 57 has an external thread for turning it into internal thread 19 of the counterbore to secure the receptacle 22 in the tube casing 13. This ring member 57 provides on its axially opposite faces reaction surfaces for engaging a resilient sealing element which is generally designated by the reference numeral 58 and serves as a yieldable or compressible diaphragm and a sealing device. Element 58 may be any rubber-like material which is compatible with the dielectric medium used between the sleeve and receptacle. The annular resilient fluid expansion and contraction accommodating diaphragm or element 58 has a generally U-shaped cross sectional shape and its rims terminate in integral annular rings 59 and 60 which serve as o-ring seals. One may see that when externally threaded metal ring member 57 is screwed tightly into the internal thread 19 of the tube casing counterbore 17, o-ring portion 59 will be compressed to effect a seal between ring member 57 and the end face of the flange 26 on receptacle 22. Also, when clamping nut 47 is turned in, the flange 27' on receptacle 27 will compress o-ring portion 60 of u-shaped element 58 to effect a seal between the flange 27' and the metal ring member 57. The u-shaped configuration of resilient element 58 allows for a free but sealed off space 61 to be created between the inside of the annular u-shaped resilient element 58 and the threaded metal ring member 57. The air-filled space 61 reduces in volume when resilient element 58 is subjected to fluid pressure on its outside surface 62 which is interfaced with and subject to any pressure developed in the dielectric fluid that resides in clearance space 35. Dielectric fluid volume changes are accommodated by flexing of the resilient u-shaped diaphragm 58. When the outside surface 62 of the diaphragm is subjected to pressure, the captured air in space 61 reduces in volume and attains a pressure that is always in equilibrium with the externally applied fluid pressure. When the dielectric medium cools and contracts, expansion of the diaphragm and the compressed air makes up for the loss in volume which would otherwise occur due to contraction to thereby prevent formation of any air or vacuum cavities in the dielectric fluid.

FIG. 5 illustrates another embodiment of the new connector assembly. Parts which are substantially the same as in the previously described embodiments are given the same reference numerals. In FIG. 5, the flange of female receptacle 22 is pressed against a shoulder on apparatus casing 13 and an o-ring forms a seal between these two parts to prevent leakage of dielectric oil from the apparatus casing. Radially extending flange 27' on the male sleeve is axially spaced from the flange 26 on the receptacle 22. Tightening of threaded locking ring 47 into casing 13 presses the flange 27' of sleeve 27 toward the flange 26 of receptacle 22. An externally threaded metal ring 65 is interposed between the two flanges. It secures receptacle 22 in the tube casing 13. The bore of ring 65 has another metal ring 66 within it. The two concentric rings form a chamber 67 in which there is a quad ring 68 that is exposed on one side to the dielectric medium in clearance space 35 between male sleeve 27 and female receptacle 22. Quad ring 68 is composed of a resilient rubber-like material. The four rims or projections from the quad ring form seals. An o-ring 69 forms a seal between interfacing surfaces on ring 65 and the flange on receptacle 22.

The quad ring 68 is yieldable for accommodating volume changes in the dielectric medium in space 35 between sleeve 27 and receptacle. A circular spring 70 with a wavy or otherwise formed cross section as shown in FIG. 6 is interposed between flange 27' of sleeve 26 and inside axially yieldable ring 66 to accommodate volume changes in chamber 67. When the dielectric medium expands, quad ring 68 and metal ring 66 slide a little bit axially and load wave spring 70 slightly. When the dielectric medium cools and contracts, the stored energy in wave spring 70 forces ring 66 and quad ring 68 axially to thereby keep the dielectric medium under compression so that no vacuum or air cavities will form in the medium. It should be evident that an o-ring, not shown, could be used in place of the quad ring seal 68.

Although the preferred FIG. 2 embodiment uses a bellows 54 in an annular chamber or cavity 55 which leads to the fluid filled clearance space 35, it should be understood that resilient or compressible elements other than a bellows may be used to compensate for dielectric fluid volume changes with temperature. For instance, a sealed tubular ring of elastic material, not illustrated, may be used in place of the bellows. A ring composed of compressible sponge may also be used but care must be exercised in choosing a sponge material that does not have a propensity to take on a permanent set when it is compressed and subjected to heat from the dielectric fluid and the surroundings at the same time.

Although several embodiments of the new anticavitation high voltage cable connector have been shown and described in considerable detail, such description is intended to be illustrative rather than limiting, for the invention may be variously embodied and is to be limited only by interpretation of the claims which follow.

We claim:

1. A high voltage cable connector including a receptacle comprising a generally tubular insulating body that is closed at one end and open at its opposite end and has a radially extending surface surrounding its open end, an insulating cable terminal sleeve having a body portion for fitting into said receptacle with an interspace remaining between the sleeve and the receptacle for being occupied by a fluid dielectric medium, said sleeve having a radially extending surface secured in spaced apart relation relative to said radially extending surface on the receptacle when the sleeve is inserted in the receptacle,
means for providing a seal between said radially extending surfaces, and
the improvement comprising a compressible and expansible element disposed between said sleeve and receptacle in contact with the dielectric medium in said interspace for compressing and expanding with thermally induced increasing and decreasing, respectively, volumetric changes of the medium.

2. The connector as in claim 1 wherein said sleeve and receptacle have thermal expansion properties, respectively, which result in maintaining the volume of said interspace nearly constant as temperature of the sleeve and receptacle change.

3. The connector as in any of claims 1 or 2 wherein said compressible and expansible element comprises bellow means.

4. A high voltage cable connector including a receptacle comprising a generally tubular insulating body that is closed at one end and open at its opposite end and has a radially extending surface surrounding its open end, an insulating cable terminal sleeve having a body portion for fitting into said receptacle with an interspace remaining between the sleeve and the receptacle for being occupied by a fluid dielectric medium, said sleeve having a radially extending surface secured in spaced apart relation relative to said radially extending surface on the receptacle when the sleeve is inserted in the receptacle, in combination with a device for preventing formation of cavities in the fluid dielectric medium, said device comprising:
sealing means disposed between said radially extending spaced apart surfaces on said sleeve and said receptacle, an annular chamber defined between said sleeve and receptacle, said chamber being connected to the dielectric medium accommodating interspace between said sleeve and receptacle, and an annular compressible and expansible element disposed in said chamber for compressing and expanding correspondingly with changes in the volume of the medium due to temperature changes in the medium and to any change in the volume of the interspace due to differential thermal expansion and contraction of the receptacle and sleeve.

5. The connector as in claim 4 wherein said compressible and expansible means is a bellows.

6. The connector as in claim 4 wherein said compressible and expansible means is a toroidal bellows surrounding said sleeve.

7. The device as in claim 4 including a ring member having axially opposite end surfaces interfacing, respectively, with said radially extending surfaces on said sleeve and receptacle and said sealing means comprising an annular pliable sealing element disposed between interfacing surfaces, said annular chamber being formed in said ring member.

8. The device as in claim 7 wherein said pliable sealing elements are quad rings.

9. The device as in claim 4 wherein said annular compressible and expansible means is an element having a u-shaped cross sectional portion constituting a diaphragm extending across said chamber for one side of said diaphragm to be exposed to said dielectric medium in said interspace and for the other side of said diaphragm to be exposed to air confined by said sealing means.

10. The device as in claim 9 including a ring member interposed between said radially extending surfaces of said sleeve and receptacle and wherein said u-shaped element has opposite edges formed as integral o-rings, respectively, one of the o-rings being for effecting said seal with said radially extending surface on the sleeve and the other of the o-rings being for effecting said seal with said radially extending surface on the receptacle.

11. The device as in claim 4 including a ring member interposed between said radially extending surfaces of said sleeve and receptacle circumjacent said sleeve, said ring member having an inside diameter greater than the outside diameter of said sleeve so as to define an annular space between said ring member and said sleeve, said compressible and expansible means comprising a ring disposed for sliding axially in said annular space, said ring having one of its axial ends exposed at one end of said ring member and the other of its axial ends spaced from the other end of said ring member for defining said chamber which is connected with said dielectric containing interspace, an axially movable sealing element disposed in said chamber for effecting a seal between said ring element and said sleeve and spring means interposed between said radially extending surface on said sleeve and said ring.

* * * * *